(12) United States Patent
Ozawa et al.

(10) Patent No.: US 6,217,510 B1
(45) Date of Patent: Apr. 17, 2001

(54) ENDOSCOPES AND ENDOSCOPE DEVICES WHICH IMAGE REGULAR OBSERVATION IMAGES AND FLUORESCENT IMAGES AS WELL AS WHICH PROVIDE EASIER OPERATION OF TREATMENT TOOLS

(75) Inventors: Takeshi Ozawa, Tama; Hitoshi Ueno, Hachioji; Sakae Takahana, Sagamihara; Nobuyuki Doguchi; Isami Hirao, both of Hino; Mamoru Kaneko, Hanno; Makoto Tomioka, Hachioji; Takefumi Uesugi, Hachioji; Yasukazu Kogen, Hachioji; Masahiro Kawauchi, Hachioji; Katsuichi Imaizumi, Hachioji; Tadashi Hirata, Hachioji, all of (JP)

(73) Assignee: Olympus Optical Co., Ltd. (JP)

(*) Notice: Subject to any disclaimer, the term of this patent is extended or adjusted under 35 U.S.C. 154(b) by 0 days.

(21) Appl. No.: 09/165,787

(22) Filed: Oct. 2, 1998

(30) Foreign Application Priority Data

Oct. 2, 1997 (JP) ................................................. 9-270049
Oct. 14, 1997 (JP) ................................................. 9-280755

(51) Int. Cl.[7] ................................................. A61B 1/05
(52) U.S. Cl. .................... 600/129; 600/128; 600/130; 600/160
(58) Field of Search ................................. 600/109, 160, 600/128, 129, 130, 476

(56) References Cited

U.S. PATENT DOCUMENTS

| | | | |
|---|---|---|---|
| 4,821,117 | * | 4/1989 | Sekiguchi ............................... 600/160 |
| 5,445,157 | * | 8/1995 | Adachi et al. ......................... 600/109 |
| 5,494,483 | | 2/1996 | Adair ..................................... 600/111 |
| 5,749,830 | * | 5/1998 | Kaneko et al. ........................ 600/160 |
| 5,772,580 | * | 6/1998 | Utsui et al. ............................ 600/160 |

FOREIGN PATENT DOCUMENTS

8-252218    10/1996   (JP).

* cited by examiner

Primary Examiner—John P. Leubecker
(74) Attorney, Agent, or Firm—Ostrolenk, Faber, Gerb & Soffen, LLP

(57) ABSTRACT

At the tip of an insertion part of an endoscope, an object window for regular observation use is positioned at almost the center, directly connected to which, said object window for fluorescent observation use is provided, and at the both sides of the object window for regular observation use and the object window for fluorescent observation use, two illumination windows are provided. A forceps hole which is an opening part at the tip side of a forceps channel which is inserted into the insertion part is provided at the lower right of the object window for regular observation use, and a treatment tool which is inserted through a forceps insertion channel is to be extruded from this forceps hole. By this way, on monitor images at both of white light observation and fluorescent observation, the treatment tool such as a forceps or the like is designated at almost the same position to improve the manipulation capability.

16 Claims, 7 Drawing Sheets

THE DIRECTION DESIGNATED TOWARD THE UPPER PART OF THE MONITOR SCREEN

THE DIRECTION DESIGNATED TOWARD THE UPPER PART OF THE MONITOR SCREEN

REGULAR OBSERVATION IMAGE

FLUORESCENT OBSERVATION IMAGE

REGULAR OBSERVATION IMAGE

FLUORESCENT OBSERVATION IMAGE

ENDOSCOPES AND ENDOSCOPE DEVICES WHICH IMAGE REGULAR OBSERVATION IMAGES AND FLUORESCENT IMAGES AS WELL AS WHICH PROVIDE EASIER OPERATION OF TREATMENT TOOLS

BACKGROUND OF THE INVENTION

1. Field of the Invention

The present invention relates to endoscopes and more specifically to endoscopes and endoscope devices which are characterized by the orientation of plural images to their forceps opening when observing an object with plural images.

2. Description of the Related Art

Recently, a technology is known that autofluorescence from organisms or fluorescence of drugs which are injected into organisms is detected by, for example, an endoscope or the like as two-dimensional images. Diagnostic analysis can be performed on degeneration of vital tissues and disease conditions (for example, types of the diseases and the infiltrated areas) of cancers or the like.

When a light is illuminated onto a vital tissue, a fluorescence with a longer wavelength than that of the excitation light is generated. As fluorescent substances existing in organisms, for example, NADH (nicotineamide adenine dinucleotide), FMN (Flavin mononucleotide), pyridine nucleotide and the like can be mentioned. Recently, the interrelationship between such biological, endogenous substances and diseases has been increasingly made clear. In addition, since HpD (hematoporphyrin), Photofrin, and ALA (δ-amino levulinic acid) show clustering activities towards cancers, by injecting the substance into an organism and then observing the fluorescence of the substance, the disease area can be diagnosed.

Because such a fluorescence is extremely subtle, an extremely high-sensitive projection is essential for the observation. A device to conduct this high-sensitive projection is described, for example, in Japanese Unexamined Patent Publication No. 8-252218. Fluorescent observation endoscope devices possess a fluorescent observation endoscope having CCDs which are provided with an imaging element to image under a white illumination and image intensifiers, such as super high-sensitive imaging elements to image subtle autofluorescence which emits from an observation object under an illumination of a light with a band from ultra-violet to blue.

In accordance with such fluorescent observation endoscopes, regular observation under a white light and autofluorescent observation can be conducted selectively or consecutively, and much more information on the observation object can be offered to examiners compared to the conventional endoscope devices.

In general, is provided for an endoscope, a forceps channel in introducing treatment tools such as a forceps and the like to the tip of the endoscope so that biopsy or excision of lesion parts within an observation object can be conducted under the endoscopic observation.

In terms of the conventional fluorescent observation endoscopes, however, no description has made on positional relationship among an objective window for white light regular observation use, an objective window for fluorescent observation use, both of which exist at the tip part of the endoscope, and a forceps hole.

For example, in a conventional fluorescent observation endoscope, as shown in FIG. 10, when an object window for regular observation use 201 and an object window for fluorescent observation use 202 are disposed to be in the upper and lower position, respectively, at the tip plane of the endoscope in the figure, illumination windows 203a and 203b are individually provided near the object window for regular observation use 201 and the object window for fluorescent observation use 202, respectively. Further, a forceps hole 204 which is an opening part at the tip side of a forceps channel is disposed between the object window for regular observation use 201 and the illumination window 203a, A nozzle 205 for washing the object window for regular observation use 201 and the object window for fluorescent observation use 202 is disposed almost in the middle, as shown in FIG. 11 and FIG. 12. In a white observation image (FIG. 11), the forceps 206 appears the lower left on the monitor screen, while in a fluorescent observation image (FIG. 12), the forceps 206 appears from the upper left on the monitor screen.

In other words, because in some cases, in both of the regular observation images and the fluorescent observation images, treatments are conducted by the forceps 206 and the like, when the position of the forceps 206 on the monitor screen is different between the regular observation images and for the fluorescent observation images, a problem occurs that this situation throws operators into confusion.

In addition, endoscopes which are used for diagnosis based on regular observation images and fluorescent observation images are formed to selectively conduct the regular observation under a white light illumination and the fluorescent observation, to observe fluorescence which is emitted from a vital tissue under an illumination of an ultraviolet-to-blue light, by means of imaging means which are installed in or connected to the endoscope. Plural examples for these endoscopes are described in Japanese Unexamined Patent Application 8-252218.

The first example has a construction where two kinds of image-formation optical systems each for the regular observation use and for fluorescent observation use are disposed in parallel. Two kinds of solid imaging elements to convert the images from these image-formation optical systems into electric signals are provided at the tip or in the operation part of the endoscope. Under illumination by a white light and an excitation light which are transferred from a light source device in a time shared way, the imaging signals which are outputted from the individual solid imaging elements are selected for conditioning and designation in accordance with the timing controls on the illumination lights.

In the second example, an object optical system which is common to the regular observation and the fluorescent observation and a beam splitter which divides the regular observation image and the fluorescent observation image which are both emitted from the object optical system into two directions based on their wavelengths are provided at the tip part of an endoscope. Solid imaging elements which individually image the regular observation image and the fluorescent observation image which have been separated by the beam splitter are installed at the tip part or in the operation part of the endoscope.

But, because in the first endoscope device of Japanese Unexamined Patent Application 8-252218, the object optical system for regular observation use and the object optical system for fluorescent observation use are provided at the tip part of the endoscope in parallel, the field of visions differ between the processes of the regular observation and the fluorescent observation. Therefore, by switching the regular observation image to the fluorescent observation image and vice versa, the field of vision of these images, which are designated on the monitor, differ each other, resulting in the problem that operators experience confusion.

Also, with the second endoscope device of Japanese Unexamined Patent Application 8-252218, due to the reflex action of the beam splitter, the regular observation image and the fluorescent observation image have a mirroring relationship, so that a special signal conditioning to reverse one of the images needs to be essential.

SUMMARY OF THE INVENTION

The present invention provides an endoscope which can designate the treatment tools such as forceps or the like at almost the same position on the monitor screen for both of the processes of a white light observation and a fluorescent observation to improve the operating capabilities.

The endoscope of the present invention has an illumination window which emits a regular observation light and a fluorescent observation light from the tip plane of the insertion part which is inserted into body cavities. An observation window is provided where a regular observation image and a fluorescent observation image derived from said regular observation light and fluorescent observation light are injected. A forceps opening part which communicates to a forceps channel which is provided within the insertion part at the tip plane of the insertion part. An imaging means which images said regular observation image and the fluorescent image are injected from the observation window with an orientation where the forceps opening part is positioned at the same direction in both of the images. The imaging means allows an operator to designate treatment tools such as a forceps and the like at almost the same position in the monitor screen at both of the processes of the white light observation and the fluorescent observation by imaging the regular observation image and the fluorescent observation image which are injected from the observation window with an orientation where the forceps opening part is positioned at the same direction. This improves the operating capabilities.

The other characteristics and advantages of the present invention will be sufficiently clear with the help of the following illustrations.

BRIEF DESCRIPTION OF THE DRAWINGS

FIG. 1 is a block diagram of an endoscope device according to the present invention; FIG. 2 is a block diagram to show the construction at the tip plane of the insertion part of the endoscope of FIG. 1; FIG. 3 is a block diagram to show the construction of the first modification example at the tip plane of the insertion part of the endoscope of FIG. 1; FIG. 4 is a block diagram to show the construction of the second modification example at the tip plane of the insertion part of the endoscope of FIG. 1; FIG. 5 is an explanatory drawing to explain the operation of the endoscope of FIG. 1; FIG. 6 is the second explanatory drawing to explain the operation of the endoscope of FIG. 1.

FIG. 8 is a block diagram to show the construction of an endoscope device, and; FIG. 9 is a cross section to show the construction of a fluorescent camera to be used for a modification example of the endoscope device of FIG. 8.

FIG. 10 is a block diagram to show the construction at the tip plane of the insertion part of the conventional endoscope; FIG. 11 is the first explanatory drawing to explain the operation of the conventional endoscope of FIG. 10, and; FIG. 12 is the second explanatory drawing to explain the operation of the conventional endoscope of FIG. 10.

DESCRIPTION OF THE PREFERRED EMBODIMENTS

Figure 1:
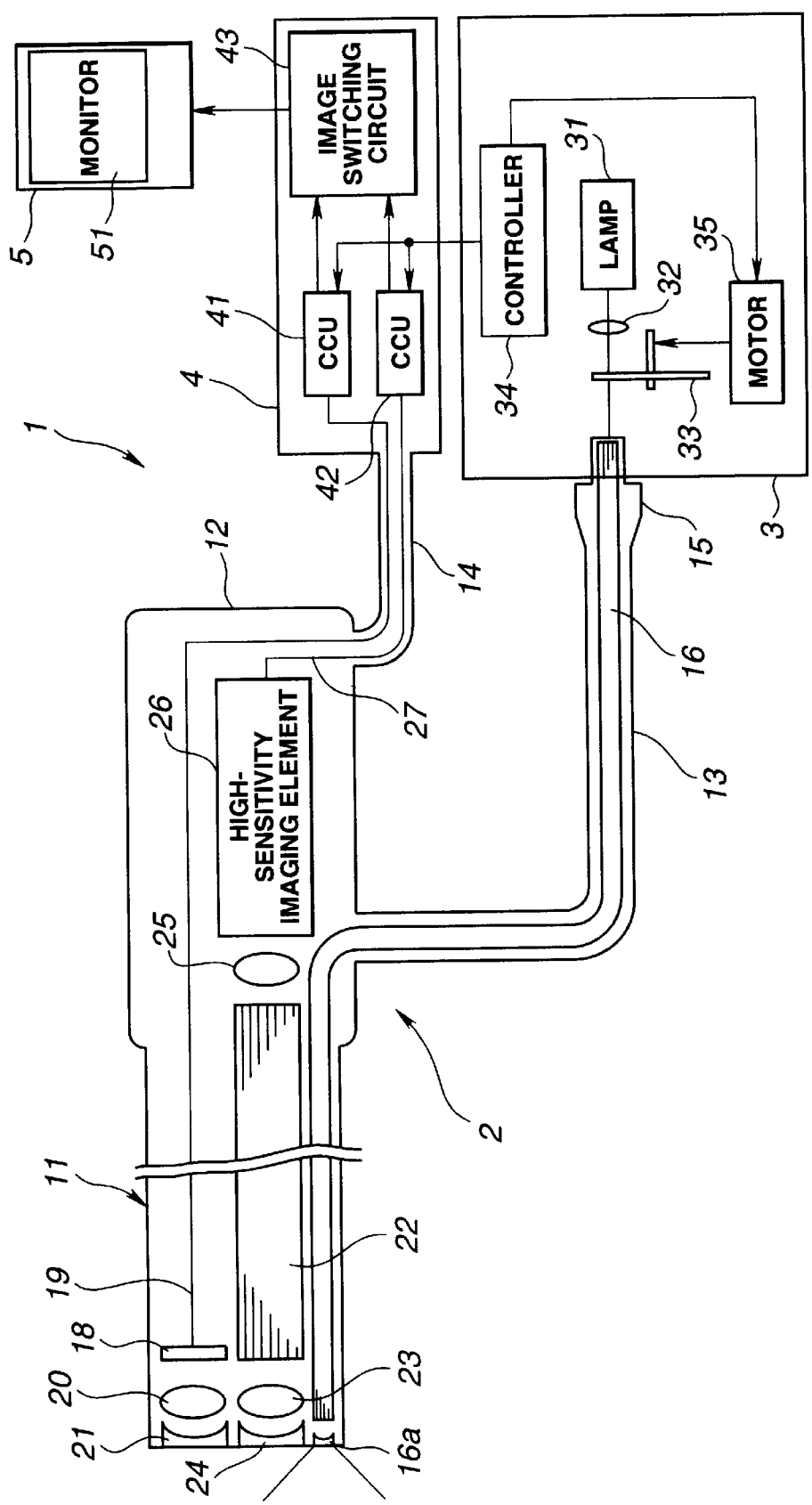
FIG. 1 to FIG. 6 are concerning the first embodiment of the present invention.

The first embodiment:

In this embodiment, as shown in FIG. 1, an endoscope device 1 has a construction where an endoscope 2 is inserted into a body cavity and then obtains a regular observation image and a fluorescent observation image for an observation part such as an affiliated part. A light source device 3 supplies illumination lights to the endoscope 2. A signal conditioning device 4 images the signals obtained by means of the endoscope 2, and a monitor 5 designates the endoscopic images generated by the signal conditioning device 4.

The endoscope 2 is composed of a slender insertion part 11 which is inserted into a body cavity. An operation part 12 is provided at the proximal end of the insertion part 11. A light guide cable part 13 extends from the operation part 12 and is connected to the light source device 3 in a removable way. A signal cable part 14 is connected to the signal conditioning device 4 in a removable way.

Further, a light guide connector 15 at the tip of the light guide cable part 13 is connected to the light source device 3 in a removable way to the tip of the insertion part 11. A light guide fiber 16 transfers the illumination light from the light source device 3 is integral. An illumination window 16a is provided at the tip part of the insertion part 11 at the side of the radiation end of this light guide fiber 16.

Also, a solid imaging element 18 to conduct the regular observation under a white light illumination is provided within the tip part of the insertion part 11. From the solid imaging element 18, a signal conductor to transfer signals to the signal conditioning device 4 is provided. At the tip part of the insertion part 11 which is in front of the imaging plane side of the solid imaging element 18, an object lens for regular observation use 20 and an object window for regular observation use 21 both in order to form images of observation parts at the solid imaging element 18 are provided.

In the insertion part 11, an image guide fiber for fluorescent observation use 22 is provided to be juxtaposed with the light guide fiber 16. At the tip part of the insertion part 11 at the tip the of said image guide fiber 22, an object lens for fluorescent observation use 23 and an object window for fluorescent use 24 are provided. And at the proximal side of the image guide fiber 22 within the operation part 12, a lens 25 and a high-sensitivity imaging element 26 in order to, image fluorescent images at the observation parts which are transferred by the image guide fiber 22 are provided. From the high-sensitivity imaging element 26, a signal conductor 27 to transfer signals to the signal conditioning device 4 is provided.

Signal conductors 19 and 27 are inserted in the signal cable part 14, and are then connected to the signal conditioning device 4 through this signal cable part 14.

Furthermore, a duct line, called a forceps channel, in order to insert a forceps and the like, is provided within the insertion part 11 (although it is not shown in FIG. 1) in the same way as regular endoscopes, and both of its proximal side and tip side have their individual openings at the operation part 12 and the tip plane of the insertion part 11, respectively. In addition, a water supply duct line, in order to supply washing water to wash the object window for regular observation window use 21 and the object window for fluorescent observation use 24, is provided within the L4 insertion part 11 (although it is also not shown in FIG. 1) in the same way as regular endoscopes.

In the light source device 3, a high intensity lamp 31 of xenon, metal halide, or the like is provided so that a light can be injected into the light guide fiber 16 through a condensing lens 32. Moreover, a band pass filter (which is not shown in the figure) which transmits only lights of blue band is provided between the high intensity lamp 31 and the light guide fiber 16 in a removable way by means of a rotary disc 33.

This rotary disc is operated by a motor 35 which is controlled by a controller 34. Therefore, in accordance with the control of the controller 34, when the band pass filter is inserted on the light path, only lights of blue band are inserted into the light guide fiber 16. When the band pass filter is withdrawn from the light path, a white light is injected into the light guide fiber 16.

The signal conditioning device 4 integrates a CCU for regular observation use 41 to image the signals from solid light imaging element 18 and a CCU for fluorescent observation use 42 to imaging signals from high-sensitive imaging element 26. Also an image switching part 43 to selectively output the imaging signals from the CCU for regular observation use 41 and the CCU for fluorescent observation use 42 is integrated therein.

Then the signals which are outputted from the image switching part 43 are transferred into the monitor 5, so that the images of the tip of the endoscope are designated on a screen 51 of the monitor 5.

Figure 2:
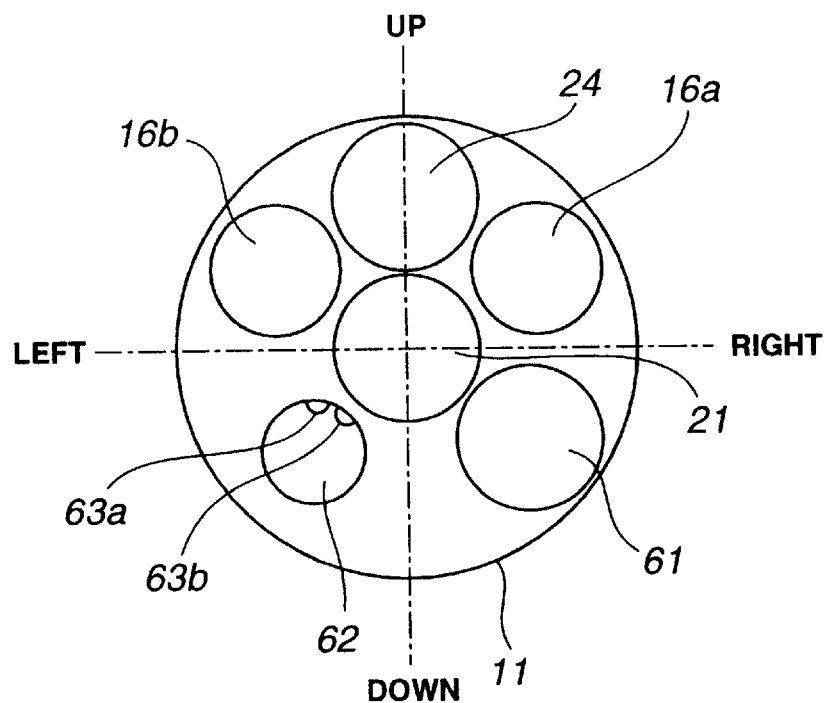

As shown in FIG. 2, at the tip of the insertion part 11, the object window for regular observation use 21 is disposed at almost the middle, and next to which, the object window for fluorescent observation use 24 is provided at the upper part of the figure.

And at both sides of the object window for regular observation use 21 and the object window for fluorescent observation use 24, illumination windows 16a and 16b are provided. This is because light guide fiber 16 is divided into two at the tip of the insertion part 11 for preventing uneven illumination, and then at both tips the illumination windows 16a and 16b are provided, respectively.

A forceps hole 61 which is an opening part at the tip side of the forceps channel which is inserted into the insertion part 11 is provided at the lower right of the object window for regular observation use, so that a treatment tool which is inserted through the forceps insertion channel is extruded from the forceps hole 61.

Also, a nozzle 62 which is an end part at the tip side of the water supply duct line is disposed at the lower left of the object window for regular observation use 21, and at the nozzle 62, two opening parts 63a and 63b are provided which form openings at the two positions so that washing water can be sprayed towards the object window for regular observation use 21 and the object window for fluorescent observation use 24.

Figure 3:
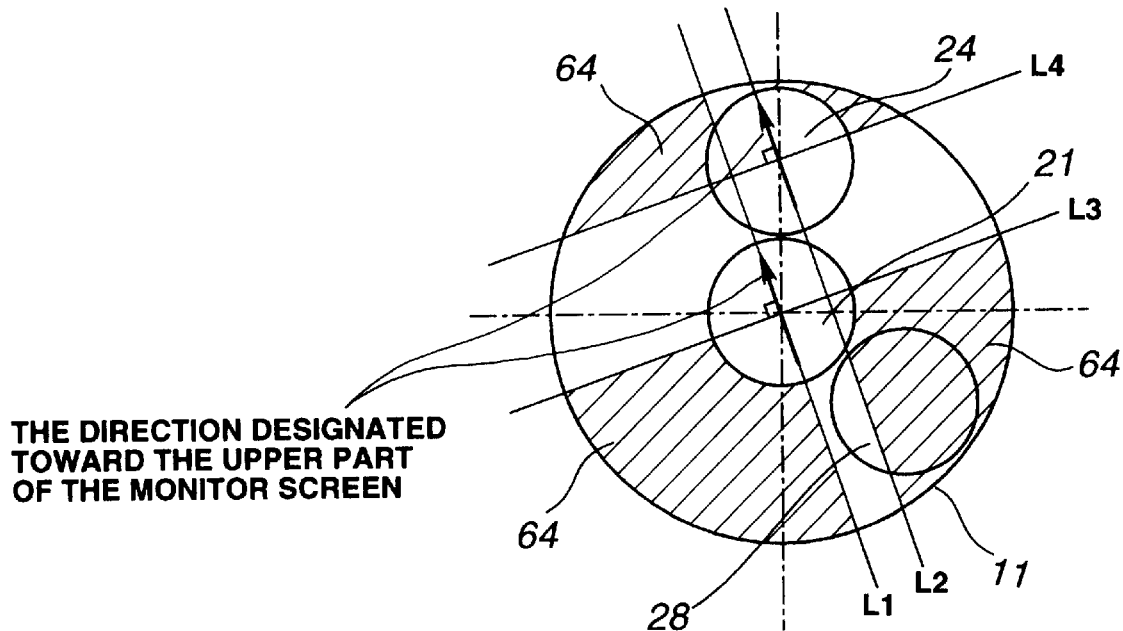

Forceps hole 61 may be not always disposed in the arrangement shown in FIG. 2, and at least, for example, as shown in FIG. 3, when lines which go through the centers of the object window for regular observation use 21 and the object window for fluorescent observation use 24 and which directions are the same as the up-and-down direction of images which are designated represent L1 and L2, respectively, and in the same way, when the normals of L1 and L2 which go through the centers of the object window for regular observation use 21 and the object window for fluorescent observation use 24 represent L3 and L4, respectively, the center of the forceps hole 61 may be disposed to be within a region 64 which is shown with slanting lines.

Figure 4:
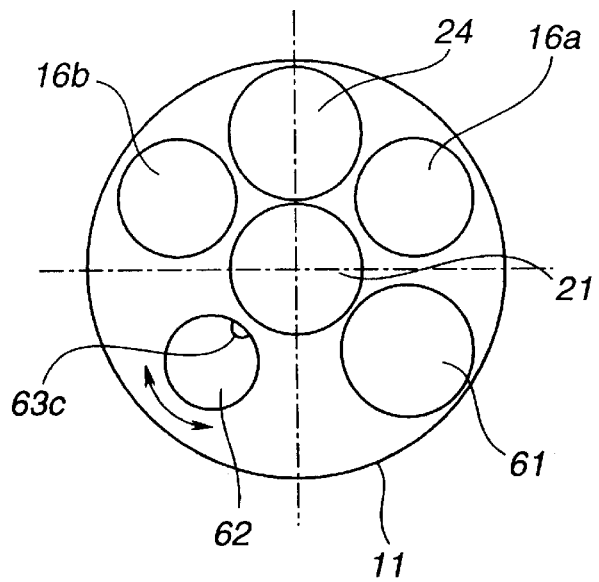

As shown in FIG. 4, a construction may be formed where an opening part 63c is provided as a single opening for the nozzle in terms of the nozzle 62. The nozzle 62 is provided in a rotatable way, so that washing water can be sprayed towards the object window for regular observation use 21 and the object window for fluorescent observation use 24.

The operation of the embodiment which has such a construction will be illustrated.

First, the insertion part 11 of the endoscope 2 is inserted into the body of a patient while observing under a white light illumination.

Under the condition of the white light observation, in the light source device 3, the band pass filter on the rotary disc 33 is in its condition of withdrawal from the optical path by means of the controller 34, and the white light which is emitted from the high intensity lamp 31 is injected into the light guide fiber 16 to illuminate the observation area at the tip of the insertion part 11.

Under the condition where the white light is emitted from such a light source device 3, the CCU for regular observation use 41 existing within the signal conditioning device 4 turns into the operating condition by means of the control signals from the controller 34 existing within the light source device 3. Then the image of the observation area at the tip of the insertion part 11 is formed as an image and then imaged at the solid imaging element 18 by the observation window for regular observation use 21 and the object lens for regular observation use 20. The signal of the solid imaging element 18 is converted into an imaging signal by the CCU for regular observation use 41, transferred to the monitor 5 through the image switching part 43. Then the regular observation image is projected at the screen 51.

When it is confirmed that the insertion part 11 reaches the area of interest for the fluorescent observation by the regular observation by means of the endoscope 2, an operator switches the condition into the fluorescent observation condition.

Under the fluorescent observation condition, the band pass filter on the rotary disc 33 is inserted into the optical path by means of the signal from the controller 34 existing within the light source device 3. Then only blue lights which transmit the band pass filter are injected into the light guide fiber 16 to illuminate the area of interest. The fluorescence which is excited from the area of interest due to the blue lights is introduced from the object window for fluorescent observation use 24 through the image guide fiber 22 to the high-sensitivity imaging element 26 existing within the operation part of the endoscope and then imaged. Then, the signal which is obtained at the high-sensitivity imaging element 26 is converted into the imaging signal at the CCU for fluorescent observation use 42 existing within the signal conditioning device 4, and then the fluorescent image is designated on the screen 51 of the monitor 5.

Solid imaging element 18 and high-sensitivity imaging element 26 existing within the insertion part 11 are disposed and arranged in an orientation where the UP direction shown in FIG. 2 is designated at the upper direction of the screen 51 of the monitor 5. Therefore, when the white light regular observation is switched to the fluorescent observation, and also when the fluorescent observation is switched to the white light regular observation, images with almost the same field of vision are designated on the screen 51 of the monitor 5.

When biopsy or ablation of the observation object tissue is carried out in the process of the white light observation an d the fluorescent observation, with inserting treatment tools from the forceps insertion opening of the op e ration part 11 of the endoscope 2 and then extruding them from the forceps hole 61, the operation is carried out while watching the endoscopic image which is projected on the screen 51 of the monitor 5.

Furthermore, when comparing the regular observation image and the fluorescent observation image, in terms of the regular observation image, because a relatively bright image can be obtained, the operations such as a treatment and the like becomes easier. On the other hand, with the fluorescent observation image, it is characterized in that because an image which includes the functional information on the tissue which can not be seen with the regular observation image, a specific area can be easily detected. Therefore, in order to carry out accurate biopsy or ablation, it is effective to conduct the operation while switching between the white light regular observation and the fluorescent observation.

Figure 5:
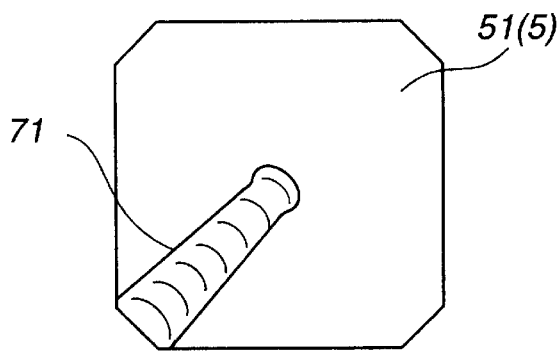
Figure 6:
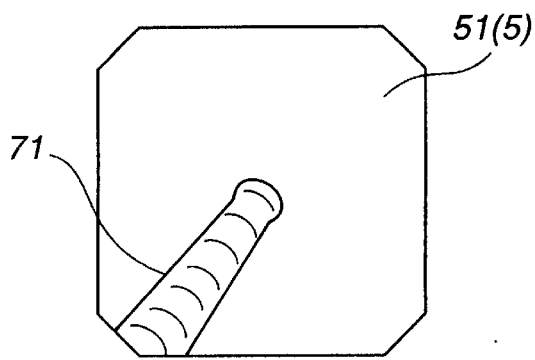

In this embodiment, by displacing the forceps hole 61 in regard to the object window for regular observation use 21 and the object window for fluorescent observation use 24 as shown in FIG. 2, in any of the regular observation image (FIG. 5) and the fluorescent observation image (FIG. 6) which are designated on the screen 51 of the monitor 5, a treatment tool 71 which is inserted from the forceps insertion opening of the operation part 11 and then extruded from the forceps hole 61 is designated at almost the same position so that the operator can conduct the treatment without any confusions.

In other words, since at any of the processes of the white light regular observation and the fluorescent observation, the treatment tool is designated at almost the same position of the endoscopic image on the monitor screen, even if the treatment is conducted with switching both of the observation images, the operator will not be troubled with any confusions as well as be able to accurately manipulate the treatment tool.

Figure 7:
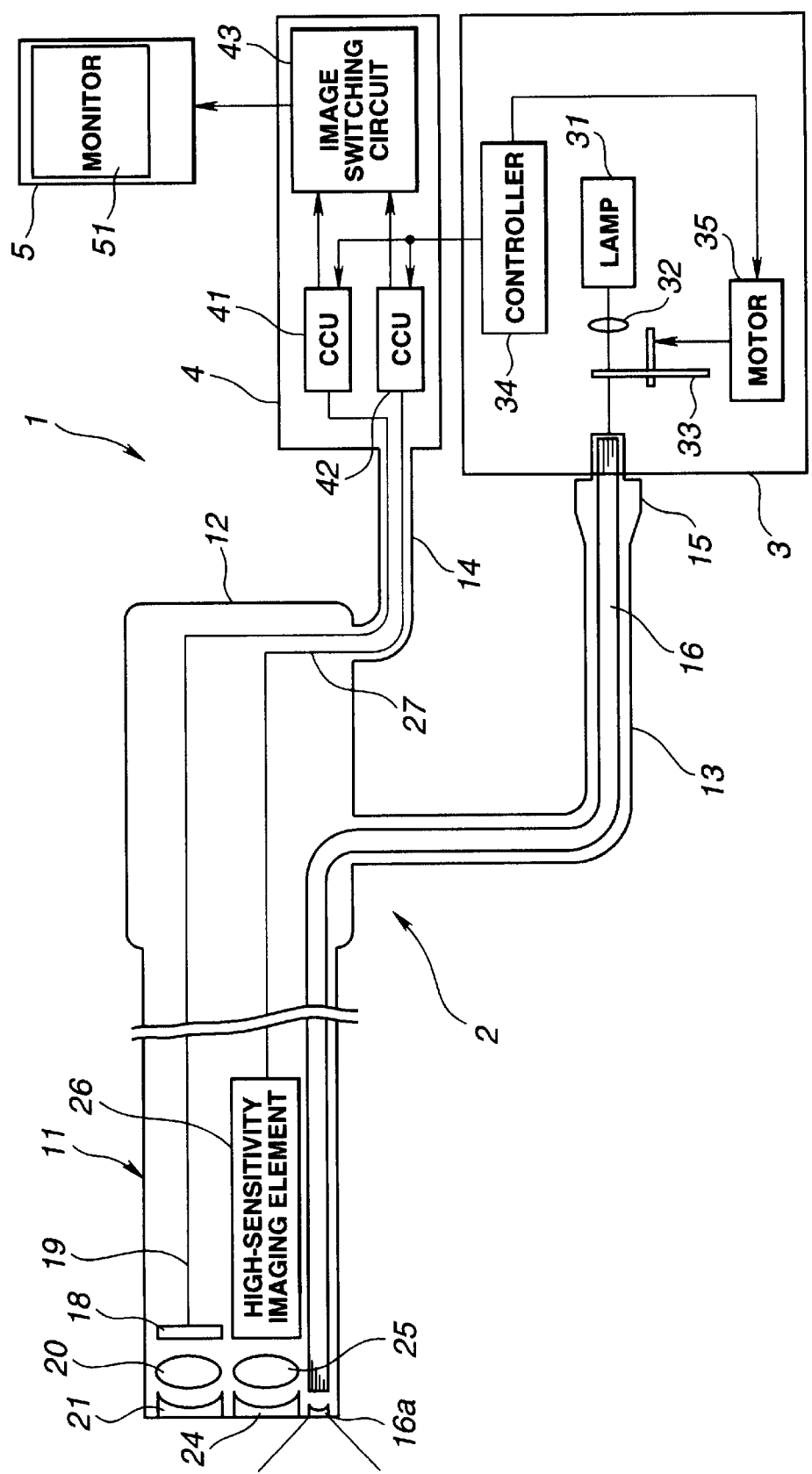
FIG. 7 is a diagram to show the construction of a modification example of the endoscope of FIG. 1.

Although in this embodiment, a construction is formed where the lens 25 and the high-sensitivity imaging element 26 are disposed at the proximal end of the image guide fiber 22 so that the fluorescent image at the observation area which is transferred by the image guide fiber 22 is imaged by the high-sensitivity imaging element 26, as shown in FIG. 7, the lens 25 and the high-sensitivity imaging element 26 may be provided within the tip part of the insertion part 11 so that the fluorescent observation image which is injected from the object window for fluorescent observation use 24 is imaged by the high-sensitivity imaging element 26.

Figure 8:
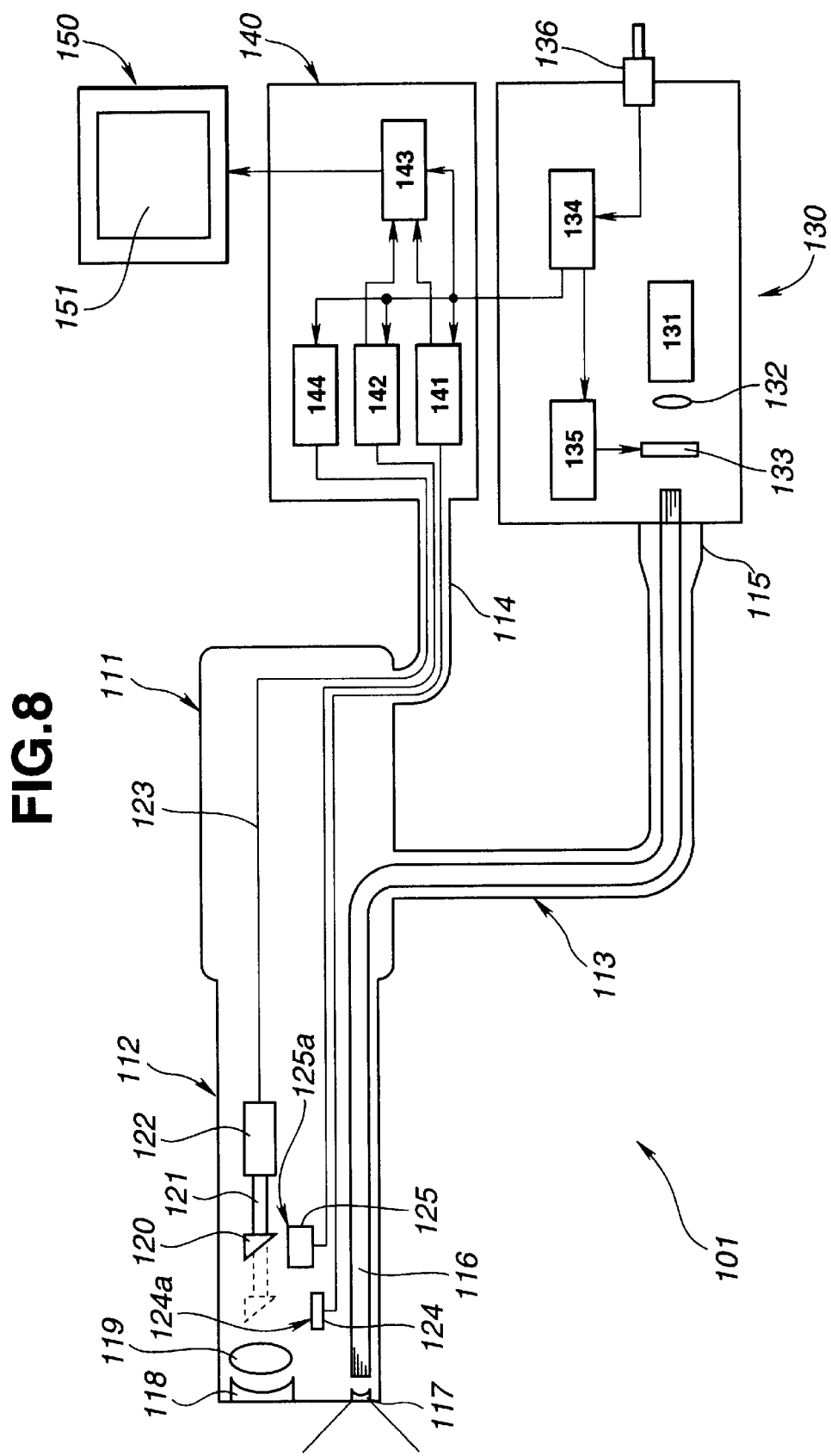
FIG. 8 and FIG. 9 concern the second embodiment of the present invention.

The second embodiment:

As shown in FIG. 8, an endoscope device 101 is composed of an endoscope main body 110, a light source device 130 which provides an illumination light to the endoscope main body 110, a signal conditioning device 140 which images an imaging signal which is obtained from the endoscope main body 110, and a monitor device 150 which designates the endoscopic image.

The endoscope main body 110 is composed of an operation part 111 to conduct insertion operations and treatment operations, and also to direct part of signal conditioning, a slender insertion part 112 which is inserted into a body cavity, the light guide cable part 113 which introduces an illumination light from the light source device 130 to the endoscope main body 110, and a signal cable part 114 which transfers the imaging signal from the endoscope main body 110 to the signal conditioning device 140.

At the side of the light source device 130 of the light guide cable part 113, the light guide connector 115 in order to connect both of which is provided. The light guide fiber 116 is integrated from the light guide connector 115 to the tip of the insertion part 112 through the insides of the light guide cable part 113, the operation part 111 and the insertion part 112. At the tip side of the insertion part 112, an illumination window 117 is disposed opposite to the tip side of the light guide fiber 116.

At the tip of the insertion part 112, an observation window 118 is disposed and at the back side thereof, an image-formation optical system 119 to form the endoscopic image is provided.

At the optical axis on the radiation side of the image-formation optical system 119, a prism 120 which converts the optical path by 90° degrees is provided. The prism 120 is fixed at the linear actuator 122 through a support 121. The linear actuator 122 can shift the prism 122 along the optical axis of the image-formation optical system 119 to steadily position the prism 120 at either of the two positions shown with the solid line and the broken line in the figure. As such a linear actuator 122, a peizo-actuator which is driven by a peizo-electric element (the one which possesses an inch-worm mechanism or the one which is driven by an ultrasonic motor mechanism are best suitable), or an electrostatic actuator which utilizes electrostatic force is suitable. From the linear actuator 122, an electric wire 123 to control the driving thereof is provided and extended to a signal conditioning device 140.

On the image-formation plane of the image-formation optical system 119 which exists at the optical path which is converted by the prism 120 which is positioned at the position shown with the broken line in the figure, a solid imaging element 124 to conduct the regular observation is disposed. The normal of the receiving plane 124a of the solid imaging element 124 is disposed to cross at right angle with the longitudinal direction of the insertion part 112.

On the image-formation plane of the image-formation optical system 119 which exists at the optical path which is converted by the prism 120 which is positioned at the position shown with the solid line in the figure, a high-sensitivity imaging element 125 to conduct the fluorescent observation is disposed. Since fluorescent observation images have lower intensities compared with those of regular observation images, it is suitable to use an imaging element which possesses amplification functions, for example a CMD (Charge Modulation Device) or the like as the high-sensitivity imaging element 125.

The normal of the receiving plane 125a of the solid imaging element 125 is disposed to cross at right angles with the longitudinal direction of the insertion part 112.

In the light source device 130, a high intensity lamp 131 such as a Xenon lamp, a metal halide lamp or the like is provided. The light which is generated by the high intensity lamp 131 is injected into the end plane of the light guide fiber 116 through a condensing lens 132.

Between the high intensity lamp 131 and the end plane of the light guide fiber 116, a band pass filter which transmits only lights with a blue band is provided in a removable manner by means of a rotary disc 133. This rotary disc 133 is driven by the motor 135 which is controlled by a controller 134. The driving control of the motor 135 by the controller 134 is conducted based on the direction signals which are inputted from the regular/fluorescence observation changing switch 136 into the controller 134. Moreover, although in FIG. 7, the regular/fluorescence observation changing switch 136 is provided in the light source device 130, it may be provided in the operation part 111 of the endoscope main body 110, or may be formed as an independent foot switch. These cases are highly suitable for operations in terms of the operations, because the operator can conduct the switching operation while conducting the observation operation of the endoscope main body 110.

By means of the above-mentioned construction of the light source device 130, when the above-mentioned band pass filter is inserted into the optical path, only lights with a blue band are injected into the light guide fiber 116, and when the band pass filter is withdrawn from the optical path, a white light is injected therein.

In the signal conditioning device 140, the signal conditioning part for regular observation use 141 which images the imaging signal from the solid imaging element 124 and the signal conditioning part for fluorescent observation use 142 which images the imaging signal from the high-sensitivity imaging element 125 are integrated, and both of which are connected to the solid imaging element 124 and the high-sensitivity imaging element 125 through electric wires, respectively.

The picture signals which the signal conditioning part for regular observation use 141 and the signal conditioning part for fluorescent observation use 142 output are inputted into the image switching part 143. In the image switching part 143, the selection signal which selects either the regular observation or the fluorescent observation, which the controller 134 generates based on the direction signal from the regular/fluorescent observation changing switch 136 is inputted, and the picture signals of the signal conditioning part for regular observation use 141 and the signal conditioning part for fluorescent observation use 142 are selected to output therein.

The signal conditioning part for regular observation use 141 and the signal conditioning part for fluorescent observation use 142 have individual driving circuits (which are not shown in the figure) which supply the driving signals to the solid imaging element 124 and the high-sensitivity imaging element 125, respectively.

Moreover, in the signal conditioning device 140, the drive control part 144 which drives the linear actuator 122 is integrated and it generates prism driving signals to position the prism 120 onto the position which is shown with the above-mentioned broken line or the solid line.

In addition, the above-mentioned selection signal is also connected to the signal conditioning part for regular observation use 141 and the signal conditioning part for fluorescent observation use 142, and is subject to the ON/OFF control of the signal output operation of the driving circuit of the corresponding signal conditioning part and the imaging element in accordance with the type of the observation image which the selection signal represent (in other words, the regular observation image and the fluorescent observation image).

The imaging signal which is outputted from the image switching part 143 is transferred to the monitor device 150 and then designated onto the screen 151.

The operation of this embodiment is illustrated as follows:

First, a certain signal is transferred from the controller 134 to each part to turn the endoscope device 101 into the regular observation mode. Then, the insertion part 112 is inserted into a body, while observing it under the white light illumination.

With the regular observation mode, the above-mentioned band pass filter of the light source device 130 is in the condition of its withdrawal from the optical path, so that the white light which is radiated from the high intensity lamp 131 is injected into the light guide fiber 116 and then illuminates the object from the illumination window 117 which is provided at the tip of the insertion part 112.

Under the condition where the white light is radiated from the light source device 130, by the selection signal from the controller 134 within the light source device 130, the prism 120 is positioned at the position which is shown with the broken line of the figure. Therefore, the endoscopic image from an object forms an image on the solid imaging element 124 through the observation window 118, the image-formation optical system 119 and the prism 120.

By means of the selection signal from the controller 134 within the light source device 130, the signal conditioning part for regular observation use 141 and the solid imaging element 124 which is integrated therein is set in its operation condition.

Accordingly, the endoscopic image which is formed on the solid imaging element 124 is converted into the imaging signal and then inputted into the signal conditioning part for regular observation use 141. After conversional conditioning into-the imaging signal is transferred into the monitor device 150 through the image switching part 143 and the regular observation image is projected onto the screen 151.

When it is desired that the fluorescent observation is conducted after the tip of the insertion part 112 reaches the observation area of interest, the operator turns the endoscope device into the fluorescent observation mode by means of the regular/fluorescent observation changing switch 136.

In the fluorescent observation mode, the band pass filter is inserted into the optical path between the high intensity lamp 131 and the light guide fiber 116 by the signal from the controller 134, and only the blue light which transmits the band pass filter is injected into the light guide fiber 116 to illuminate the object.

In the fluorescent observation mode, by the selection signal from the controller 134 within the light source device 130, the prism 120 is positioned at the position which is shown with the solid line in the figure. Therefore, the endoscopic image from the object is formed on the high-intensity imaging element 125 through the observation window 118, the image-formation optical system 119 and the prism 120.

By the selection signal from the controller 134 within the light source device 130, the driving circuit of the signal conditioning part for fluorescent observation use 142 and the high-sensitivity imaging element 125 which is integrated therein is set in its operation condition.

Accordingly, the endoscopic image which is formed at the high-sensitivity imaging element 125 is converted into the imaging signal and then inputted into the conditioning part for fluorescent observation use 142, and after the conversional conditioning into the picture signal, is transferred into the monitor device 150 through the image switching part 143, and then the fluorescent observation image is projected onto the screen 151.

With the endoscope device 101 according to this embodiment, an endoscopic image is formed onto the solid imaging element 124 and the high-sensitivity imaging element 125 through the same observation window 118 and the image-formation optical system 119, so that the same field of view can be obtained with both of the observation modes.

In this case, by designating the regular observation image and the fluorescent observation image onto the screen 151 of the monitor device 150 at the same size, the comparative examination can be easily conducted.

As described above, with the endoscope device 101 according to this embodiment, since the images with entirely the same field of view are designated in the processes of the regular observation and the fluorescent observation, operators will not experience confusion. Moreover, since the high-sensitivity imaging element is disposed at the tip of the insertion part of the endoscope, which is the closest position to an observation subject, bright and clear fluorescent images can be obtained.

Figure 9:
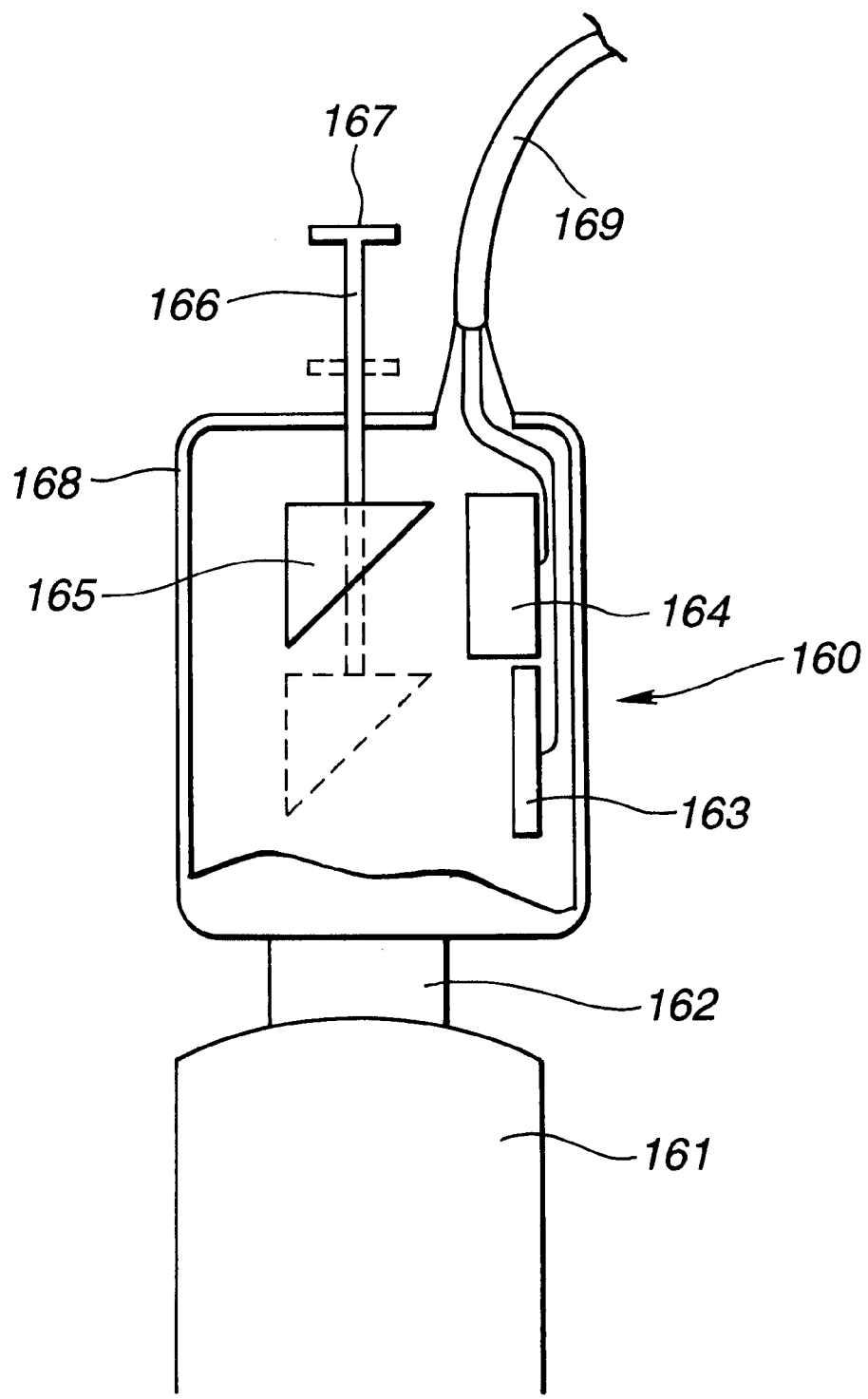
Figure 10:
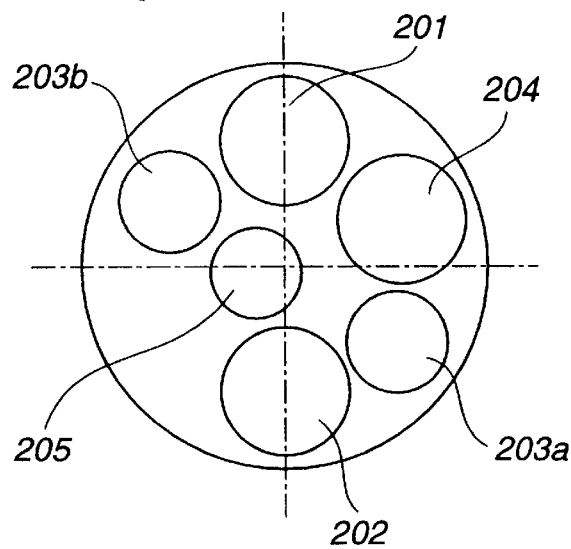
FIG. 10 to FIG. 12 concern a conventional example.
Figure 11:
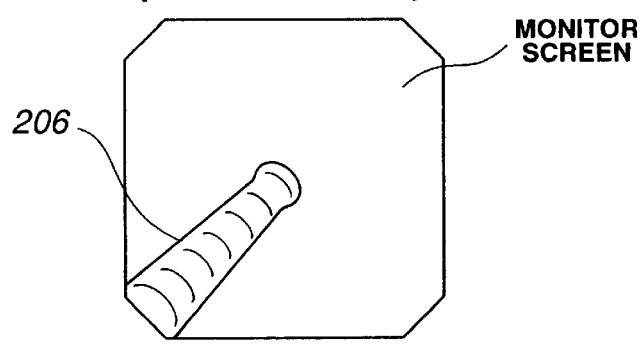
Figure 12:
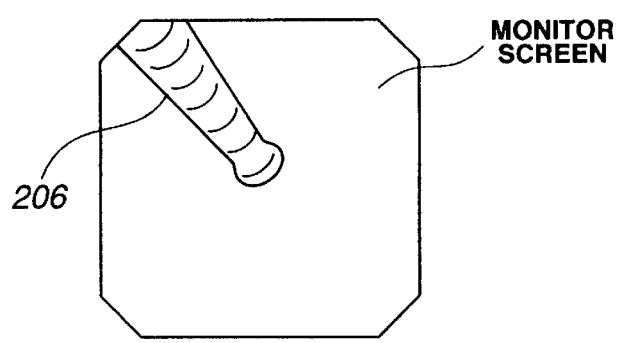

Referring to FIG. 9, one modification example according to the second embodiment will be set forth.

This modification example is an application part in the second embodiment of the optical system which is loaded at the tip of the insertion part of the endoscope onto the fluorescent observation camera which is to be installed onto the eyepiece.

As shown in FIG. 9, the fluorescent observation camera 160 according to the modification example of this embodiment is used with it mounted onto the eyepiece part 162 which is directly connected to the operation part 161 of the fiber scope. Further, the optical system within the eyepiece part 162 is movable towards the direction of the optical axis, so that it shifts when the fluorescent observation camera 160 is mounted to form the real image of the endoscopic image which is transferred to the end plane of the image guide fiber of the fiber scope onto a certain image-formation plane.

Within the fluorescent observation camera 160, the solid imaging element 163 which is used for the regular observation and the high-sensitivity imaging element 164 which is used for the fluorescent observation are provided to be juxtaposed. As the high-sensitivity imaging element, other than CMD mentioned above, a CCD where an intensifier which multiplies quantity of light is provided at its front can be used as highly suitable one.

On the optical path for the admittance light within the fluorescent observation camera 160, the prism 165 which rotates the optical path 90-degrees is provided. To the prism 165, the position adjusting lever 166 is directly connected, and at the end part of the position adjusting lever 166, the knob 167 is provided and is extended out to the housing 168 of the fluorescent observation camera 160.

By pushing in the knob 167, the prism 165 shifts to the position of the broken line of the figure and forms the endoscopic image onto the solid imaging element 163 which is provided onto the image-formation plane of the eyepiece part 162.

By pulling up the knob 167, the prism 165 shifts to the position of the solid line of the figure and forms the endoscopic image onto the high-sensitivity imaging element 164 which is provided onto the image-formation plane of the eyepiece part 162.

The electric wires which receive the operation signal and the imaging signal between the solid imaging element 163 and the high-sensitivity imaging element 164 and the individual signal conditioning parts, respectively, are in a bundle.

Since the light source device 130, the signal conditioning device 140 and the monitor device 150 are the same as those shown in FIG. 7, these illustrations will be omitted.

With the endoscope device according to this modification example, the fluorescent observation camera 160 is mounted onto the eyepiece part 162 of the fiber scope. By pushing in the knob 167, the regular observation mode is set using the regular/fluorescent observation changing switch 136 of the light source device 130.

Moreover, when the fluorescent observation is desired, with pulling up the knob 167, the fluorescent observation mode is set using the regular/fluorescent observation changing switch 136 of the light source device 130. The other operations are the same as those of the first embodiment.

In accordance with the endoscope device according to this modification example, in addition to the advantages of the endoscope device according to the second embodiment, the fluorescent observation can be conducted using a special optical system or a regular fiber scope which does not posses any imaging elements. Therefore, it is extremely economic, since the fluorescent observation can be conducted only with adding a camera to the existing apparatus. Moreover, since a variety of fiber scopes which have different lengths and/or outer diameters can be utilized, the fluorescent observation on a variety of areas of the body can be conducted.

In the present invention, it is clear that a wide variety of different embodiments can be constructed based on the present invention without escaping from the spirit and intent of the present invention. The present invention will not be limited by any specific embodiments, but restricted only by the appended clams.

What is claimed is:

1. An endoscope comprising:
   an illumination window which illuminates a white light or fluorescent excitation light from the tip plane of an insertion part which is inserted into a body cavity;
   observation windows which are provided at the tip plane of said insertion part and next to said illumination window, and where white light reflected images and fluorescent images, respectively, are received;
   an opening end of an instrument channel which is provided at the tip plane of said insertion part; and
   imaging means which images said white light reflected images and said fluorescent images which are received from said observation windows in an orientation where images of said observation windows are disposed in the same direction, wherein said observation windows are composed of a first observation window where said white light reflected images are received having a vertical direction, and a second observation window where received are said fluorescent images which have substantially the same vertical direction as said white light reflected image;
   said opening end has its center which is disposed at the position which is defined by:
   a first axis which goes through the vertical direction line of said white light reflected images which are received from said first observation window and also the center of said first observation window,
   a second axis which goes through the vertical direction line of said fluorescent images which is received from said second observation window and also the center of said second observation window,
   third axis which goes through the center of said first observation window and crosses at right angles with said first axis, and
   a fourth axis which goes through the center of said second observation window and crosses at right angles with said second axis;
   and further wherein said opening end has its center positioned within an area of the tip plane that is not in the area defined by the area between the first and second axes or the area between the third and fourth axes.

2. An endoscope according to claim 1, wherein said imaging means comprises a first solid state imaging element, and a second solid state imaging element with a higher sensitivity than that of said first imaging element.

3. An endoscope according to claim 1, wherein said imaging means is a solid state imaging element which is provided within the distal end of said insertion part.

4. An endoscope according to claim 1, wherein said endoscope has an image transferring means which transfers said fluorescent image which is received from the second observation window to the side of the proximal end of said insertion part, and said imaging means comprises a solid state imaging element which is provided within a proximal end of said insertion part to image said fluorescent image which is transferred from said image transferring means.

5. An endoscope according to claim 1, wherein said imaging means comprises a first solid state imaging element provided within the distal end of said insertion part, and a second solid state imaging element with a higher sensitivity than that of said first imaging element.

6. An endoscope according to claim 1, wherein said endoscope has an image transferring means which transfers said fluorescent image which is received from the second observation window to the side of the proximal end of said insertion part, said imaging means comprises a first solid state imaging element which is provided within the tip part of said insertion part, and a second solid state imaging element with a higher sensitivity than that of said first imaging element and is provided within the proximal part of said insertion part to image said fluorescent image which is transferred from said image transferring means.

7. An endoscope comprising:

an illumination window which illuminates a white light or fluorescent excitation light from the tip plane of an insertion part which is inserted into a body cavity;

observation windows which are provided at the tip plane of said insertion part and next to said illumination window, and where white light reflected images and fluorescent images, respectively, are received;

an opening end of an instrument channel which is provided at the tip plane of said insertion part; and imaging means which images said white light reflected images and said fluorescent images which are received from said observation window in an orientation where images of said observation window are disposed in the same direction, wherein said imaging means are composed of a first imaging means which images said white light reflected images and a second imaging means which images said fluorescent images, said observation windows are composed of a first observation window where received are said white light reflected images having a vertical direction which the first imaging means images and a second observation window where received are said fluorescent images which said second imaging means images and which have substantially the same vertical direction as that of said white light reflected images which are imaged by said first imaging means;

said opening end has its center which is disposed at the position which is defined by:

a first axis which goes through the vertical direction axis of said white light reflected images which are received from said first observation window and also the center of said first observation window;

a second axis which goes through the vertical direction axis of said fluorescent images which is received from said second observation window and also the center of said second observation window;

a third axis which goes through the center of said first observation window and crosses at right angles with said first axis; and a fourth axis which goes through the center of said second observation window and crosses at right angles with said second axis;

wherein said opening end has its center positioned within an area of the tip plane that is not in the area defined by the area between the first and second axes or the area between the third and fourth axes.

8. An endoscope according to claim 7, wherein said first imaging means and said second imaging means are solid state imaging elements, said second imaging means being a solid state imaging element with a higher sensitivity than that of said first imaging means.

9. An endoscope according to claim 7, wherein said first imaging means is a solid state imaging element which is provided within the distal end of said insertion part.

10. An endoscope according to claim 7, wherein said second imaging means is a solid state imaging element which is provided within the distal end of said insertion part.

11. An endoscope according to claim 7, wherein said endoscope has an image transferring means which transfers said fluorescent image which is received from the second observation window to the side of the proximal end of said insertion part, and said second imaging means is a solid state imaging element which is provided within the proximal end of said insertion part to image said fluorescent image which is transferred from said image transferring means.

12. An endoscope according to claim 7, wherein said first imaging means and said second imaging means are solid state imaging elements which are provided within the distal end of said insertion part, said second imaging means being a solid state imaging element with a higher sensitivity than that of said first imaging means.

13. An endoscope according to claim 7, wherein said endoscope has an image transferring means which transfers said fluorescent image which is received from the second observation window to the side of the proximal end of said insertion part, said first imaging means being a solid state imaging element which is provided within the tip apart of said insertion part, and said second imaging means being a solid state imaging element with a higher sensitivity than that of said first imaging means and is provided within the proximal part of said insertion part to image said fluorescent image which is transferred from said image transferring means.

14. An endoscope comprising:

an illumination window which illuminates a white light or fluorescent excitation light from the tip plane of an insertion part which is inserted into a body cavity;

an observation window which is provided at the tip plane of said insertion part and next to said illumination window, and where white light reflected images and fluorescent images, respectively, are received;

an opening end of an instrument channel which is provided at the tip plane of said insertion part; and imaging means which images said white light reflected images and said fluorescent images which are received from said observation window in an orientation where images of said observation window are disposed in the same direction, wherein said imaging means is composed of a first imaging means which images said white light reflected image and a second imaging means which images said fluorescent image, said images having an optical axis, and has an optical path changing means which selectively changes the optical path of the images which are received from said observation window between first and second positions on the optical axis at the proximal side of said observation window, said first imaging means is disposed at a position where images form with said optical path changing means in said first position forms an image, and said second imaging means is disposed at a position where images form with said light path changing means in said second position forms an image, and wherein said first imaging means and said second imaging means are disposed within the distal end of said insertion part.

15. An endoscope according to claim 14, wherein said optical path changing means is composed of a direction changing means which changes the orientation of the optical axis of said optical path to a certain direction, and a driving means which changes the position or orientation of said direction changing means.

16. An endoscope according to claim 14, wherein said first imaging means and said second imaging means are solid state imaging elements, said second imaging means being a solid state imaging element with a higher sensitivity than that of said first imaging means.

* * * * *